(12) United States Patent
Ho et al.

(10) Patent No.: US 8,470,522 B2
(45) Date of Patent: Jun. 25, 2013

(54) THREE-DIMENSIONAL CULTURE CONTAINING HUMAN ARTICULAR CHONDROCYTES WITH INDUCED TERMINAL DIFFERENTIATION CHANGES AND PREPARATION PROCESS AND USES OF THE SAME

(75) Inventors: Mei-Ling Ho, Kaoshsiung (TW); Gwo-Jaw Wang, Taipei (TW); Je-Ken Chang, Kaohsiung (TW)

(73) Assignee: Kaohsiung Medical University (TW)

( * ) Notice: Subject to any disclaimer, the term of this patent is extended or adjusted under 35 U.S.C. 154(b) by 900 days.

(21) Appl. No.: 11/490,860

(22) Filed: Jul. 20, 2006

(65) Prior Publication Data

US 2008/0026362 A1 Jan. 31, 2008

(51) Int. Cl.
*C12Q 1/00* (2006.01)
*C12N 15/07* (2006.01)
*A61K 35/32* (2006.01)

(52) U.S. Cl.
USPC ............................... 435/4; 435/366; 424/548

(58) Field of Classification Search
None
See application file for complete search history.

(56) References Cited

PUBLICATIONS

Fragonas, E. et al "Articular cartilage repair in rabbits by using suspensions of allogenic chondrocytes in alginate" Biomaterials, 2000, 21(8), pp. 795-801.*
Christelle Sanchez, Marguarida M Mateus, Marie-Paule Defresne, Jean-Michel R Crielaard, Jean-Yves L Reginster, and Yves E Henrotin "Metabolism of human articular chondrocytes cultured in alginate beads. Longterm Effects of Interleukin-1beta and Nonsteroidal Antiinflammatory Drugs" J Rheumatol,2002,29(4),pp. 772-782.*
Chubinskaya, S; Huch, K; Schulze, M; Otten, L; Aydelotte, MB; Cole, AA "Human Articular Chondrocytes Cultured in Alginate Beads Maintain Their Gene Expression" Cells and Materials, 1998, 8, pp. 151-160.*
Stevens, DA and Williams, GR "Hormone Regulation of Chondrocyte Differentiation and Endochondral Bone Formation" Molecular and Cellular Endocrinology, 1999, 151 (1-2), pp. 195-204.*
Abyad, A. et al.; "Arthritis and aging"; 1992, *Curr. Opin. Rheumatol.*, vol. 4, No. 2, pp. 153-159.
Adam, M. et al.; "Altered expression of collagen phenotype in osteoarthrosis"; 1983, *Clinica Chimica Acta*, vol. 133, pp. 25-32.
Adams, Christopher S. et al.; "Chondrocyte Apoptosis Increases with Age in the Articular Cartilage of Adult Animals"; 1998, *The Anatomical Record*, vol. 250, pp. 418-425.
Aigner, Thomas et al.; "Independent Expression of Fibril-forming Collagens I, II, and III in Chondrocytes of Human Osteoarthritic Cartilage"; 1993, *J. Clin. Invest.*, vol. 91, pp. 829-837.
Blanco, Francisco J. et al.; "Chondrocyte Apoptosis Induced by Nitric Oxide"; 1995, *American Journal of Pathology*, vol. 146, No. 1, pp. 75-85.
Blanco, Francisco J. et al.; "Osteoarthritis Chondrocytes Die by Apoptosis: A Possible Pathway for Osteoarthritis Pathology"; 1998, *Arthritis & Rheumatism*, vol. 41, No. 2, pp. 284-289.
Domm, C. et al.; "Redifferentiation of dedifferentiated bovine articular chondrocytes in alginate culture under low oxygen tension"; 2002, *Osteoarthritis and Cartilage*, vol. 10, pp. 13-22.
Hashimoto, Sanshiro et al.; "FAS/FAS Ligard Expression and Induction of Apoptosis in Chondrocytes"; 1997, *Arthritis & Rheumatism*, vol. 40, No. 10, pp. 1749-1755.
Hashimoto, Sanshiro et al.; "Chondrocyte Apoptosis and Nitric Oxide Production During Experimentally Induced Osteoarthritis"; 1998, *Arthritis & Rheumatism*, vol. 41, No. 7, pp. 1266-1274.
Hashimoto, Sanshiro et al.; "Linkage of Chondrocyte Apoptosis and Cartilage Degradation in Human Osteoarthritis"; 1998, *Arthritis & Rheumatism*, vol. 41, No. 9, pp. 1632-1638.
Heraud, F. et al.; "Apoptosis in normal and osteoarthritic human articular cartilage"; 2000, *Ann. Rheum. Dis.* vol. 50, pp. 959-965.
Ho, Mei-Ling et al.; "A novel terminal differentiation model of human articular chondrocytes in three-dimensional cultures mimicking chondrocytic changes in osteoarthritis"; 2006 *Cell Biology International*, vol. 30, pp. 288-294.
Horton, Walter E. et al.; "Chondrocyte Apoptosis in Development, Aging and Disease"; 1998, *Matrix Biology*, vol. 17, pp. 107-115.
Kirsch, T. et al.; "Activation of annexin II and V expression, terminal differentiation, mineralization and apoptosis in human osteoarthritic cartilage"; 2000, *Osteoarthritis and Cartilage*, vol. 8, pp. 294-302.
Kronenberg, Henry M.; "Developmental regulation of the growth plate"; 2003, *Nature*, vol. 423, pp. 332-336.
Long, Fanxin et al.; "Genetic manipulation of hedgehog signaling in the endochondral skeleton reveals a direct role in the regulation of chondrocyte proliferation"; 2001, *Development*, vol. 128, pp. 5099-5108.
Lotz, M. et al.; "Osteoarthritis and Cartilage"; 1999, *Osteoarthritis and Cartilage*, vol. 7, pp. 389-391.
Malda, J. et al.; "Expansion of human nasal chondrocytes on marcoporous microcarriers enhances redifferentiation"; 2003, *Biomaterials*, vol. 24, pp. 5153-5161.
Malda, J. et al.; "Expansion of Bovine Chondrocytes on Microcarriers Enhances Redifferentiation"; 2003, *Tissue Engineering*, vol. 9, No. 5, pp. 939-948.
Noonan, Kenneth J. et al.; "Changes in Cell, Matrix Compartment, and Fibrillar Collagen Volumes between Growth-Plate Zones"; 1998, *Journal of Orthop. Res.*, vol. 16, pp. 500-508.
Shum, Lillian et al.; "The life cycle of chondrocytes in the developing skeleton"; 2002, *Arthritis Res.*, vol. 4, pp. 94-106.
Walker, Cheryl et al.; "5-Azacytidine-Induced Uncoupling of Differentiation and Tumorigenicity in a Murine Cell Line"; 1984, *JNCI*, vol. 73, No. 4, pp. 877-884.
Zuscik, Michael J. et al.; "5-Azacytidine Alters TGF-β and BMP Signaling and Induces Maturation in Articular Chondrocytes"; 2004, *Journal of Cellular Biochemistry*, vol. 92, pp. 316-331.

\* cited by examiner

*Primary Examiner* — Chris R Tate
*Assistant Examiner* — Aaron J Kosar
(74) *Attorney, Agent, or Firm* — Kilpatrick Townsend & Stockton LLP

(57) ABSTRACT

Disclosed herein is a three-dimensional culture containing human articular chondrocytes with induced terminal differentiation changes, as well as a process for preparing the same. The three-dimensional culture, which was found to mimic the biological characteristics of articular chondrocytes that undergo terminal differentiation in vivo, can be used as a tool in the studies of the molecular and cellular mechanisms of osteoarthritis, and in the screening of candidate drugs for use in treatment of a disorder associated with articular chondrocytes.

21 Claims, 3 Drawing Sheets

THREE-DIMENSIONAL CULTURE CONTAINING HUMAN ARTICULAR CHONDROCYTES WITH INDUCED TERMINAL DIFFERENTIATION CHANGES AND PREPARATION PROCESS AND USES OF THE SAME

BACKGROUND OF THE INVENTION

1. Field of the Invention

This invention relates to a three-dimensional culture containing human articular chondrocytes with induced terminal differentiation changes, as well as the preparation process and uses of said culture.

2. Description of the Related Art

Osteoarthritis (OA) is a joint disease with a gradual degradation of articular cartilage, especially in the aged population (D. Hamerman (1995), Ann Rheum Dis., 54:82-85). Previous reports indicated that 10% of the elderly population (more than 60 years old) suffered from OA in the United States (D. Hamerman (1989), N Engl J Med., 320:1322-1330; G. Peat et al. (2001), Ann Rheum Dis., 60:91-97). Furthermore, a previous report indicated that females with OA mostly suffered from the onset of the symptoms of OA at peri-menopausal stage (M. Y. Nadkar et al. (1999), J Assoc Physicians India, 47:1161-1163). Therefore, it is quite necessary to study the strategies for preventing disease progress at the early stage of OA.

Several previous studies from OA patients indicated that the biological characteristics of articular chondrocytes during the progress of OA included terminal differentiation, mineralization and eventually apoptosis (F. J. Blanco et al. (1998), Arthritis Rheum, 41:284-289; F. Heraud et al. (2000), Ann Rheum Dis, 59:959-965; T. Kirsch et al. (2000), Osteoarthritis Cartilage, 8:294-302). Osteoarthritic chondrocytes were found to express annexin, alkaline phosphatase (ALP) and collagen type X (also called collagen X)(T. Kirsch et al. (2000), Osteoarthritis Cartilage, 8:294-302). Expressions of collagen type X and annexin V reflect the characteristics of hypertrophic chondrocytes as a mature differentiation. Chondrocytic apoptosis was also found in OA cartilage, and it has been suggested that chondrocytic apoptosis might be associated with the decrease of cellularity and abnormal mineralization in OA cartilage (F. J. Blanco et al. (1998), Arthritis Rheum, 41:284-289; S. Hashimoto et al. (1998b), Proc Natl Acad Sci USA, 95:3094-3099; F. Heraud et al. (2000), Ann Rheum Dis, 59:959-965). Accordingly, investigators indicated that the osteoarthritic articular chondrocytes resume the genetic and phenotypic characteristics that were similar to the terminal differentiation of chondrocytes in epiphyseal growth-plates (T. Kirsch et al. (2000), Osteoarthritis Cartilage, 8:294-302). One of the prospects of managing OA is to suppress the terminal differentiation of articular chondrocytes and eventually stop the disease progress in the very early stage of OA. However, studies relevant to an in vitro model applying human articular chondrocytes reaching a terminal differentiation stage for elucidating the progression mechanism of OA have not been reported.

5-azacytidine is a DNA or RNA methyl transferase inhibitor resulting in hypomethylation. It has been reported that 5-azacytidine replaced cytidine in genomic DNA during replication and thus perturbed the methylation pattern of cytidine present in various target gene promoters, such that the transcriptional repression was relieved and the cell differentiation program was changed (J. K. Christman et al. (1983). Cancer Res., 43:763-769; P. A. Jones and S. M. Taylor (1980), Cell, 20:85-93; P. A. Jones et al. (1983), J Exp Zool., 228:287-295; C. Tarella et al. (1982), Cancer Res., 42:445-449; C. Walker et al. (1984), J Natl Cancer Inst., 73:877-885). It was also reported that 5-azacytidine induced the terminal differentiation changes of cultured epiphyseal chondrocytes as occurred during endochondral ossification (J. O. Cheung et al. (2001), J Bone Miner Res., 16:309-318). In addition, M. J. Zuscik et al. established a model to study the regulation mechanism of articular chondrocyte maturation (M. J. Zuscik et al. (2004), J Cell Biochem., 92:316-331). Their study indicated that the 5-azacytidine-treated chicken articular chondrocytes were induced to express the maturational hallmarks, including collagen type X, alkaline phosphatase (ALP), and Indian hedgehog (Ihh), and showed altered collagen type X and alkaline phosphatase expression in response to bone morphogenetic protein-2 (BMP-2), transforming growth factor-$\beta$ (TGF-$\beta$), and parathyroid hormone-related protein (PTHrP). However, this model has yet to be applied to cultured human articular chondrocytes.

Alginate is a copolymer of L-guluronic acid and D-mannuronic acid that polymerizes to form a gel in the presence of calcium ions. Alginate can easily be depolymerized with the addition of a calcium chelator such as sodium citrate or EDTA. Alginate has found application in cell encapsulation, cell transplantation, and tissue engineering. Cells that are suspended in an alginate solution may be entrapped in alginate beads with three-dimensional configuration that form upon polymerization. These alginate beads can be used for in vitro culture and also for transplantation in vivo into articular cartilage defects. Previous studies using human articular chondrocytes cultured in alginate beads have shown that these human articular chondrocytes secrete a matrix similar to that seen in native human cartilage, and maintain their phenotype over long periods of time.

Based on the findings from the aforesaid studies, the applicants endeavored to develop a three-dimensional culture containing human articular chondrocytes that may be induced to reach a terminal differentiation stage, so that the three-dimensional culture containing human articular chondrocytes can act as a cell culture model mimicking the terminal differentiation occurring in osteoarthritic chondrocytes, can be used for identifying a pathology associated with articular chondrocytes, such as osteoarthritis, and can be used for screening a candidate drug in the treatment of a disorder associated with articular chondrocytes, such as osteoarthritis.

SUMMARY OF THE INVENTION

Therefore, according to a first aspect, this invention provides a three-dimensional culture containing human articular chondrocytes with induced terminal differentiation changes, the culture being prepared by a process comprising:

admixing human articular chondrocytes with an alginate solution to form a cell suspension;

dropping the cell suspension into a calcium chloride solution to result in the formation of alginate beads which have the human articular chondrocytes entrapped therein;

cultivating the alginate beads thus-formed in a medium allowing the growth of the human articular chondrocytes; and treating the cultivated alginate beads with a demethylating agent, such that terminal differentiation changes of the human articular chondrocytes entrapped in the alginate beads are induced.

In a second aspect, this invention provides a process for preparing a three-dimensional culture containing human articular chondrocytes with induced terminal differentiation changes, the process comprising:

admixing human articular chondrocytes with an alginate solution to form a cell suspension;

dropping the cell suspension into a calcium chloride solution to result in the formation of alginate beads which have the human articular chondrocytes entrapped therein;

cultivating the alginate beads thus-formed in a medium allowing the growth of the human articular chondrocytes; and treating the cultivated alginate beads with a demethylating agent, such that terminal differentiation changes of the human articular chondrocytes entrapped in the alginate beads are induced.

The three-dimensional culture containing human articular chondrocytes according to this invention can be used as a cell culture model mimicking the terminal differentiation occurring in osteoarthritic chondrocytes, can be used for identifying a pathology associated with articular chondrocytes, such as osteoarthritis, and can be used for screening a candidate drug in the treatment of a disorder associated with articular chondrocytes, such as osteoarthritis.

BRIEF DESCRIPTION OF THE DRAWINGS

The above and other features and advantages of the present invention will become apparent in the following detailed description of the preferred embodiments with reference to the accompanying drawing, of which.

DETAILED DESCRIPTION OF THE INVENTION

Figure 1:
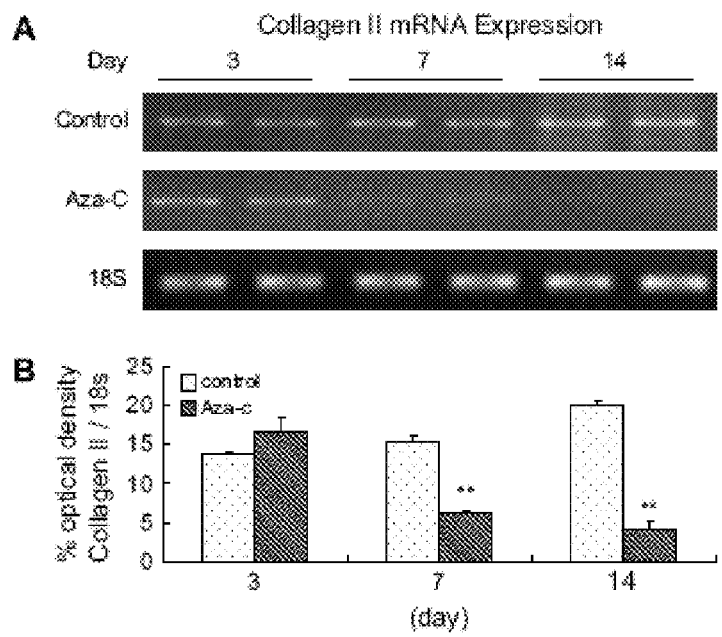
FIG. 1 shows the changes of mRNA expression of collagen type II in human articular chondrocytes on Day 3, 7 and 14 after a 48 hr treatment of 5-azacytidine (Aza-C), wherein the mRNA expression of collagen type II was semi-quantified by RT-PCR and normalized relative to the expression of 18S rRNA, in which panel A shows the representative images assessed from the control and Aza-C treated cultures, and panel B shows the calculated ratio of the optical densities of collagen type II to 18S (% optical density collagen II/18S) for comparison. Each bar represents the mean±SEM of four replicated cultures. Data were evaluated by Mann-Whitney U test; and **: $p<0.01$, as compared to the control culture of the same day after Aza-C treatment.

For the purpose of this specification, it will be clearly understood that the word "comprising" means "including but not limited to," and that the word "comprises" has a corresponding meaning.

It is to be understood that, if any prior art publication is referred to herein, such reference does not constitute an admission that the publication forms a part of the common general knowledge in the art, in Taiwan or any other country.

Unless defined otherwise, all technical and scientific terms used herein have the meaning commonly understood by a person skilled in the art to which this invention belongs.

In this invention, in order to provide a tool for studying the mechanism(s) of osteoarthritis, the applicants attempted to establish a cell culture mimicking the terminal differentiation that occurs in osteoarthritic chondrocytes. Normal articular chondrocytes obtained from human knees were treated with 5-azacytidine (Aza-C) and were harvested on Day 3, 7 and 14 after treatment, respectively. The phenotypic and genetic changes of articular chondrocytes were detected. The obtained results showed that the mRNA expression of collagen type II, a marker for normal functional articular chondrocytes, was significantly decreased after Aza-C treatment, as compared to the control cultures, while those of collagen type X and ALP, markers for hypertrophic chondrocytes, were significantly increased. In addition, the cell size and apoptotic rate of articular chondrocytes were significantly increased, as compared to the control after 14 days of Aza-C treatment. Therefore, in this invention, the applicants developed a terminal differentiation model of 3-D cultured human articular chondrocytes, which may be widely used in academic researches and in the pharmaceutics industry, e.g., for use in identifying a pathology associated with articular chondrocytes, such as osteoarthritis, and in screening candidate drugs effective in the treatment of a disorder associated with articular chondrocytes, such as osteoarthritis.

Therefore, this invention provides a three-dimensional culture containing human articular chondrocytes with induced terminal differentiation changes.

The term "terminal differentiation changes" as used herein means the human articular chondrocytes undergo at least one of the following processes: cells stop proliferating, cells become hypertrophic (cells' volume increases), and cells express collagen type X, followed by the expression of at least one of the following proteins: annexin, Indian hedgehog (Ihh) and alkaline phosphatase. Subsequently, the hypertrophic human articular chondrocytes deposit mineral and finally undergo apoptosis.

In particular, the three-dimensional culture containing human articular chondrocytes according to this invention may display at least one of the following biological characteristics: the down-regulation of the normal functional gene of human articular chondrocytes (i.e., collagen type II gene), the up-regulation of hypertrophic marker gene (i.e., collagen type X gene) and mineralization marker gene (i.e., ALP gene), and an increase in cell volume and apoptotic rate.

This invention also provides a process for preparing the aforesaid three-dimensional culture containing human articular chondrocytes, the process comprising:
  admixing human articular chondrocytes with an alginate solution to form a cell suspension;
  dropping the cell suspension into a calcium chloride solution to result in the formation of alginate beads which have the human articular chondrocytes entrapped therein;
  cultivating the alginate beads thus-formed in a medium allowing the growth of the human articular chondrocytes; and
  treating the cultivated alginate beads with a demethylating agent, such that terminal differentiation changes of the human articular chondrocytes entrapped in the alginate beads are induced.

The human articular chondrocytes used in the admixing step are obtained from an articular cartilage of a human subject, preferably a healthy human subject.

In a preferred embodiment of this invention, the articular cartilage is taken from a part of the human subject selected from a normal mature knee cartilage, and cartilages from metacarpophalargeal, radiocarpal, ankle and pelvic joints.

In a more preferred embodiment of this invention, the human articular chondrocytes used in the admixing step are obtained from a normal mature knee cartilage of a healthy human subject.

Preferably, the alginate solution used in the admixing step is a 1.2% or 2.4 sodium alginate solution in 0.9% NaCl. Alternatively, the alginate solution may be substituted by one containing a biomolecule such as collagen and gelatin that may result in the formation a scaffold in a 3-D culture system.

Preferably, the demethylating agent used in the treating step is selected from the group consisting of 5-azacytidine, 5-aza-deoxycytidine, 5'-flouro-2'-deoxycytidine, pseudoisocytidine, dihydro-5-azacytidine and arabinofuranosyl-5-azacytosine (fazarabine). In a preferred embodiment of this invention, the demethylating agent is 5-azacytidine.

In a preferred embodiment of this invention, the cultivating step is conducted at 37° C. in a humidified atmosphere of 5% $CO_2$.

In a preferred embodiment of this invention, the treating step is conducted at 37° C. in a humidified atmosphere of 5% $CO_2$.

In view of the detected biological characteristics that will be described hereinbelow, it is contemplated that the three-dimensional culture containing human articular chondrocytes according to this invention can find a variety of applications in academic researches and the pharmaceutics industry. For instance, it can be used as a cell culture model mimicking the terminal differentiation occurring in osteoarthritic chondrocytes. In addition, it can be manufactured in a form of a commercial kit for identifying a pathology associated with articular chondrocytes, such as osteoarthritis, or for screening a candidate drug in the treatment of a disorder associated with articular chondrocytes.

This invention will be further described by way of the following examples. However, it should be understood that the following examples are solely intended for the purpose of illustration and should not be construed as limiting the invention in practice.

EXAMPLES

Materials and Methods

A. Preparation of Three-Dimensional Cultures Containing Human Articular Chondrocytes
1. Origins and Cell Cultures of Human Articular Chondrocytes:
  (a) Normal human articular chondrocytes NHAC-kn (Clonic®, BioWhittaker, Walkersville, Md.) were obtained from the knee of a 50-year-old Caucasian male. According to the manufacturer's guidelines, NHAC-kn cultures were established for application to the studies of formation, breakdown and regeneration of hyaline cartilage, osteoarthritis research and the proliferation and differentiation of chondrocytes.
  (b) Normal human articular chondrocytes KMU-AC were established from fresh cadaver-knees of a 23-year-old Asian male (supplied by the Hospital of Kaohsiung Medical University) according to the following procedures: Firstly, the knee cartilages were minced and sequentially digested by hyaluronidase (0.5 mg/ml), pronase (1 mg/ml) and collagenase (1 mg/ml). The digested product was collected by centrifugation and plated in a 10 cm Petri dish containing DMEM supplemented with 10% fetal bovine serum, 0.1% ITS-premix, 1% non-essential amino acids and 0.5% penicillin-streptomycin, followed by incubation at 37° C. in an incubator with 20% $O_2$ and 5% $CO_2$. When the resultant monolayer of articular chondrocytes reached confluence, cells were detached from the bottom of the Petri dish using 0.1% trypsin-EDTA and were then sub-cultured for 4 passages. The thus-obtained sub-cultures of KMU-AC chondrocytes were used in the step of preparation of alginate beads as described below.

2. Preparation of Alginate Beads Containing Human Articular Chondrocytes:

The alginate beads were prepared with reference to C. Sanchez et al. (2002), *J. Rheumatol*, 29:772-82. Briefly, the above-described human articular chondrocyte cultures were suspended in a 1.2% alginate solution in 0.9% NaCl, so as to form a cell suspension at a density of $1\times10^6$ cells/mL. The cell suspension was then slowly dropped into a 102 mM $CaCl_2$ solution through a yellow pipette tip, to result in the formation of alginate beads entrapping the human articular chondrocytes. The thus-formed alginate beads were allowed to polymerize for further 10 minutes in the $CaCl_2$ solution at room temperature.

After washing with saline solution, 15 alginate beads were cultivated in 5 ml of culture medium per well in a 6-well plate. Culture medium was the Chondrocyte basal medium (Bulletkit, Clonic®; BioWhittaker, Walkersville, Md.) with a supplement of the Chondrocyte growth medium, containing R3-IGF1, bFGF, transferrin, insulin, fetal bovine serum and gentamicin/amphotericin-B (SingleQuots, Clonic®; Bio-Whittaker, Walkersville, Md.). The alginate beads were cultured for 7 days at 37° C. in a humidified incubator with 5% $CO_2$ and the culture medium was changed every 3 days. Cultures were then treated with 15 µg/ml of 5-azacytidine (Aza-C) (Sigma, St Louis, Mo.) for 48 hr.

3. 5-azacytidine Treatment of Alginate Beads Containing Human Articular Chondrocytes:

The cultivated alginate beads as described above were treated with 15 µg/mL of 5-azacytidine (Sigma, St Louis, Mo.) for 48 hours. Thereafter, they were maintained in media without Aza-C for another 2 weeks. Cells were harvested on Day 3, 7 and 14 after Aza-C treatment, respectively. The control cultures were cultivated and harvested under the same conditions except that the treatment of Aza-C was omitted.

Human articular chondrocytes were released from the alginate beads by dissolving the beads in a 0.9% NaCl solution containing 0.05M sodium citrate and 0.03M sodium EDTA at pH 7.4. Cells for each experiment were collected by low-speed centrifugation at 1,000 rpm for 5 min.

The NHAC-kn cultures were used in the following experiments except the quantitative real-time polymerase chain reaction (quantitative real-time PCR). The KMU-AC cultures were used to quantify mRNA expression by quantitative real-time PCR, which was performed to further confirm the effect of Aza-C on gene expression of human articular chondrocytes.

B. Reverse Transcription-Polymerase Chain Reaction (RT-PCR) Analysis:

On Day 3, 7 and 14 after a 48 hr Aza-C treatment, expressions of the mRNA of type II and type X collagens and alkaline phosphatase (ALP) of Aza-C-treated and non-treated cells (control) were measured by RT-PCR.

Total RNA was isolated from human articular chondrocytes using the Trizol reagent (Gibco BRL, Rockville, Md.). The first strand cDNA was converted from 1 µg of RNA by adding the Moloney murine leukemia virus reverse transcriptase and the oligo(dT) primer. PGR was performed using an Applied Biosystems GeneAmp 9600 PCR system (Applied Biosystems, Foster City, Calif.). The PCR reaction was carried out using specific primers of each gene under the following cycling conditions: denaturing at 94° C. for 4 min, followed by 40 cycles at 94° C. for 30 sec, annealing at 60° C. for 45 sec, and extension at 72° C. for 45 sec.

The thus-obtained PCR products (amplicons) were resolved by electrophoresis on a 1.4% agarose gel and visualised by ethidium bromide staining. The optical densities of the resolved bands were semi-quantified using a Bioimaging System (UVP Inc., Upland, Calif.). The 18S rRNA gene was used as a control gene for normalization. The optical intensity ratios of the PCR products to the 18S rRNA gene were calculated for comparison.

Table 1 shows the nucleotide sequences of the specific primers used in the RT-PCR experiment.

TABLE 1

Specific primers used in the RT-PCR experiment.

| Target gene | Primer | Sequence (5'→3') | Amplicon size (bp) |
|---|---|---|---|
| Collagen type II | F1 | aactggcaagcaaggagaca (SEQ ID NO: 1) | 621 |

TABLE 1-continued

Specific primers used in the RT-PCR experiment.

| Target gene | Primer | Sequence (5'→3') | Amplicon size (bp) |
|---|---|---|---|
| α 1 | R1 | agtttcaggtctctgcaggt (SEQ ID NO: 2) | |
| Collagen type X | F2 | agccagggttgccaggacca (SEQ ID NO: 3) | 387 |
| α 1 | R2 | ttttcccactccaggagggc (SEQ ID NO: 4) | |
| ALP | F3 | gcgaacgtatttctccagacccag (SEQ ID NO: 5) | 367 |
| | R3 | ttccaaacaggagagtcgcttcaa (SEQ ID NO: 6) | |
| 18S rRNA | F4 | ccgcagctaggaataatggaataggac (SEQ ID NO: 7) | 220 |
| | R4 | acgacggtatctgatcgtcttcg (SEQ ID NO: 8) | |

C. Quantitative Real-Time PCR Analysis:

Quantitative real-time PCR was also performed to further confirm the finding from RT-PCR. On Day 3, 7 and 14 after a 48 hr Aza-C treatment, the mRNA expressions of type II and type X collagens and ALP of Aza-C treated and control cells were measured. The procedures for total RNA isolation and the first strand cDNA conversion were the same as those for RT-PCR.

The quantitative real-time PCR was performed in an ABI Prism 7900 HT Sequence Detection System (Applied Biosystems, Foster City, Calif.) using the SYBR Green PCR Master Mix Reagent containing the Amplitaq Gold DNA polymerase, dNTP mixed with dUTP, SYBR Green 1, passive reference and reaction buffer (Applied Biosystems, Foster City, Calif.).

Reactions were performed in a 25 µL mixture containing cDNA, specific primers of each gene and the SYBR Green PCR Master Mix reagent. The cycling conditions were as follows: for collagen type IIα1, 1 cycle at 50° C. for 2 min and 95° C. for 10 min, followed by 40 cycles at 95° C. for 15 sec and 62° C. for 1 min; for collagen type Xα1, 1 cycle at 50° C. for 2 min and 95° C. for 10 min, followed by 40 cycles at 95° C. for 15 sec, 52° C. for 20 sec and 72° C. for 20 sec; for ALP and GAPDH, 1 cycle at 50° C. for 2 min and 95° C. for 10 min, followed by 40 cycles at 95° C. for 15 sec and 60° C. for 1 min.

Table 2 shows the nucleotide sequences of the specific primers used in the quantitative real-time-PCR experiment:

TABLE 2

Specific primers used in the quantitative real-time PCR experiment.

| Target gene | Primer | Sequence (5'→3') | Amplicon size (bp) |
|---|---|---|---|
| Collagen type II | F5 | caacactgccaacgtccagat (SEQ ID NO: 9) | 71 |
| α 1 | R5 | tcttgcagtggtaggtgatgttct (SEQ ID NO: 10) | |
| Collagen type X | F6 | cagatttgagctatcagaccaacaa (SEQ ID NO: 11) | 85 |

TABLE 2-continued

Specific primers used in the quantitative real-time PCR experiment.

| Target gene | Primer | Sequence (5'→3') | Amplicon size (bp) |
|---|---|---|---|
| α 1 | R6 | aaattcaagagaggcttcacatacg (SEQ ID NO: 12) | |
| GAPDH | F7 | tctcctctgacttcaacagcgac (SEQ ID NO: 13) | 126 |
| | R7 | ccctgttgctgtagccaaattc (SEQ ID NO: 14) | |
| ALP | F8 | ggaggccgaaagtacatgtttc (SEQ ID NO: 15) | 72 |
| | R8 | gaaacatgtactttcggcctcc (SEQ ID NO: 16) | |

The thus-obtained PCR products (amplicons) were detected by the fluorescence of SYBR Green, the double stranded DNA binding dye (T. B. Morrison et al. (1998), *Biotechniques*, 24:954-958, 960, 962). The relative mRNA expression level was calculated from the threshold cycle ($C_t$) value of each PCR product and normalized with that of GAPDH using comparative $C_t$ method (K. J. Livak and T. D. Schmittgen (2001), *Methods*, 25:402-408). The relative quantity of the expression of each gene from the control cells on Day 3 after the Aza-C treatment was set to 100%, and all the others were transformed to a percentage change relative thereto. After PCR reaction, a dissociation (melting) curve was generated to check the specificity of PCR reaction. All the PCR amplifications were performed in triplicate, and experiments were repeated at least 3 times.

D. Flow Cytometry:

The cell size of articular chondrocytes from the control and Aza-C treated cultures was analysed by flow cytometry on Day 14 after the Aza-C treatment. The cultured cells were released from alginate beads in the same manner as described above. Cells ($1 \times 10^6$) were then suspended in phosphate buffered saline and analysed immediately on a laser flow cytometer (EPICS Elite; Coulter, Hialeah, Fla.). The intensity in forward scatter was measured by using an argon laser (488 nm) as a probing beam. The relative intensity represents the cell size of a chondrocyte. Five to six thousand chondrocytes from the control and Aza-C treated cultures were measured. The data was analysed by the WinMDI software (EPICS Elite ESP; Beckman-Coulter Electronics, Hialeah, Fla.).

E. TUNEL (Terminal Deoxynucleotidyl Transferase Mediated dUTP Nick End Labeling) Assay:

Fragmented DNA of an apoptotic cell was TUNEL stained using an In Situ Cell Death Detection Kit, TMR red (Roche, Germany). According to the manufacturer's guidelines, on Day 14 after the Aza-C treatment, articular chondrocytes from the control and Aza-C treated cultures were fixed with 4% paraformaldehyde in phosphate buffered solution (PBS) at a cell density of $1 \times 10^6$/mL and incubated at room temperature for 10 min. After centrifugation at 200 rpm for 5 minutes, cells were fixed in 80% ethanol and then settled on a slide by centrifugation at a speed of 2,000 rpm for 5 minutes using a cytospin (Cytospin 3; Shandon, UK). Slides were rinsed twice with PBS, and cells were permeabilized by incubating in permeabilization solution (0.1% Triton X-100 in 0.1% sodium citrate) for 2 min on ice. A TUNEL reaction mixture containing terminal deoxy-nucleotidyl transferase and rhodamine (the labelling dye) was added onto the slides and incubated at 37° C. for 60 min in a humidified chamber in the dark. The reaction was stopped by the addition of a blocking buffer (0.1% TritonX-100/0.5% BSA in PBS). Cells were counter-stained by 4',6-diamidino-2-phenylindole (DAPI). Slides were observed on a fluorescence microscope with an excitation wavelength of 580 nm for rhodamine and 365 nm for DAPI. Cell nuclei were stained blue by DAPI, whereas only apoptotic cells were stained red by rhodamine. Stained cells were counted in 5 microscopic fields for each slide. Data were analyzed using Image-Pro® Plus analysis software (Media Cybernetics, Sliver Spring, Md.). The ratio of red stained cells (apoptotic cells) to blue stained cells (total cells) was defined as the apoptotic rate of chondrocytes.

F. Statistical Analysis

Data from the RT-PCR, quantitative real-time PCR and TUNEL stain experiments were expressed as the means±SEM of 4 wells from representative experiments. Statistical significance was evaluated by Mann-Whitney U test. Data from flow cytometry for cell size measurement are shown as the means±SEM of 5000-6000 cells in each group. Statistical significance was evaluated by Student's t-test. All the experiments were repeated at least three times. $p<0.05$ was considered significant (*: $p<0.05$; and **: $p<0.01$, as compared to the control group).

Results

Figure 2:
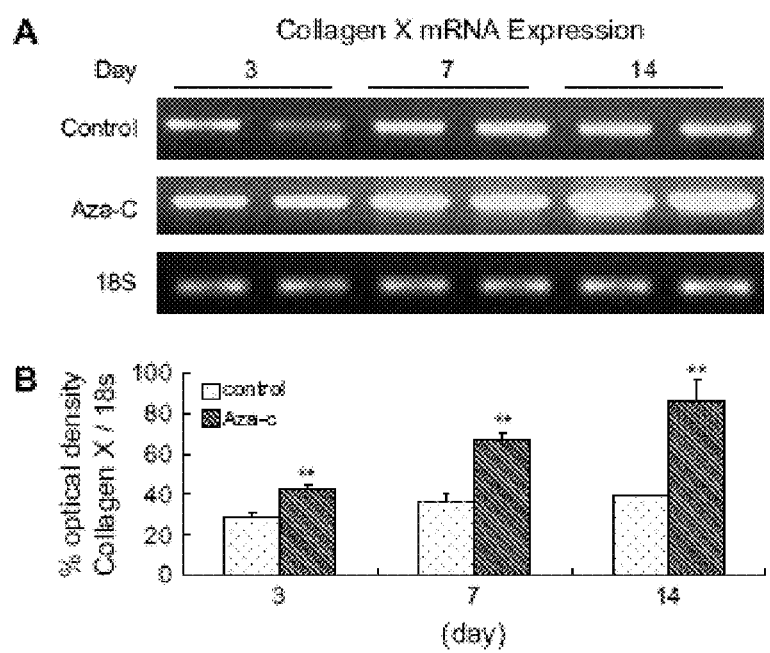
FIG. 2 shows the changes of mRNA expression of collagen type X in human articular chondrocytes on Day 3, 7 and 14 after a 48 hr treatment of Aza-C, wherein the mRNA expression of collagen type X was semi-quantified by RT-PCR and normalized relative to the expression of 18S rRNA, in which panel A shows the representative images of the bands assessed from the control and Aza-C treated cultures, and panel B shows the calculated ratio of the optical densities of collagen type X to 18S (% optical density collagen X/18S) for comparison. Each bar represents the mean±SEM of four replicated cultures. Data were evaluated by Mann-Whitney U test; and **: $p<0.01$, as compared to the control culture of the same day after Aza-C treatment.
Figure 3:
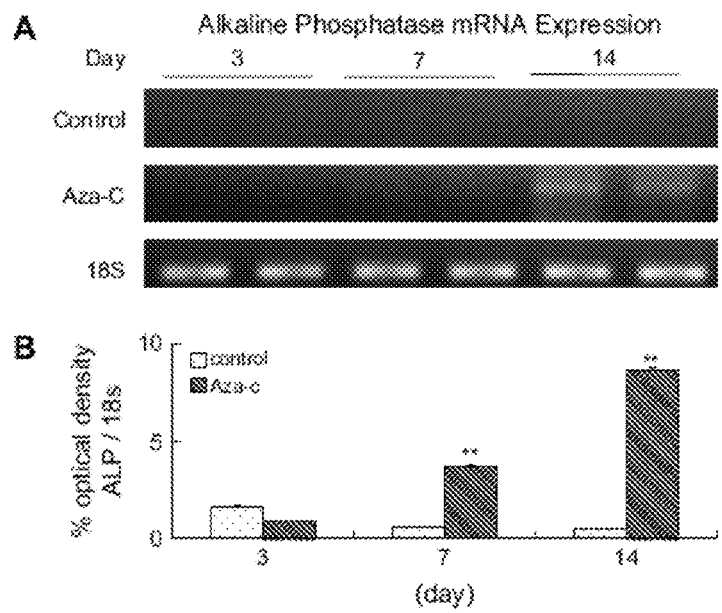
FIG. 3 shows the changes of mRNA expression of alkaline phosphatase in human articular chondrocytes on Day 3, 7 and 14 after a 48 hr treatment of Aza-C, wherein the mRNA expression of alkaline phosphatase was semi-quantified by RT-PCR and normalized relative to the expression of 18S rRNA, in which panel A shows the representative images of the bands assessed from the control and Aza-C treated cultures, and panel B shows the calculated ratio of the optical densities of alkaline phosphatase to 18S (% optical density ALP/18S) for comparison. Each bar represents the mean±SEM of four replicated cultures. Data were evaluated by Mann-Whitney U test; and **: $p<0.01$, as compared to the control culture of the same day after Aza-C treatment.

1. Reverse Transcription-Polymerase Chain Reaction (RT-PCR):

The mRNA expression levels of collagen type II gene, collagen type X gene, and alkaline phosphatase (ALP) gene in human articular chondrocytes on Day 3, 7 and 14 after a 48 hr Aza-C treatment were determined by RT-PCR. As compared to the control group, the mRNA expression of collagen type II gene in the Aza-C-treated group was significantly decreased on Day 7 ($p<0.01$) and Day 14 ($p<0.01$) after the Aza-C treatment (see panels A and B of FIG. 1), whereas the mRNA expression of collagen type X gene in the Aza-C-treated group was significantly increased on Day 3 ($p<0.01$), Day 7 ($p<0.01$) and Day 14 ($p<0.01$) after the Aza-C treatment (see panels A and B of FIG. 2). The mRNA expression of ALP gene in the Aza-C-treated group was significantly increased on Day 7 ($p<0.01$) and Day 14 ($p<0.01$) after the Aza-C treatment, whereas that of the control group was hardly detectable (see panels A and B of FIG. 3).

Figure 4:
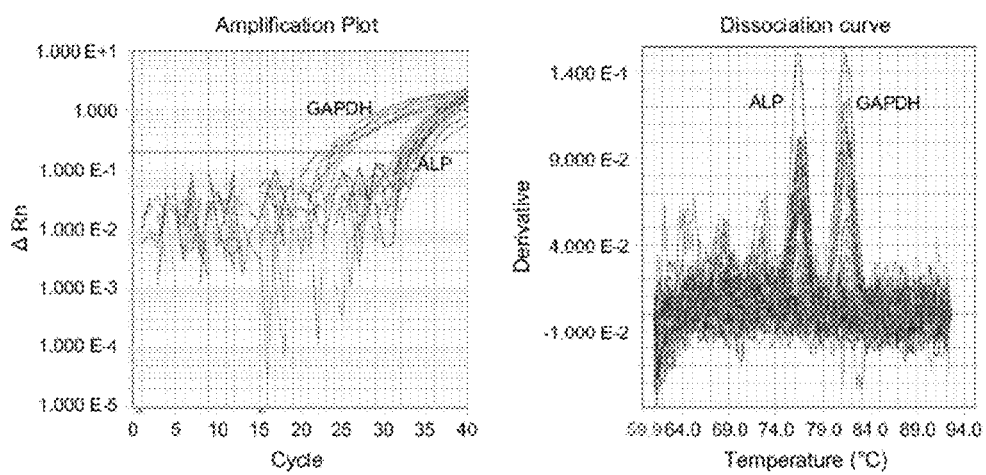
FIG. 4 shows the representative amplification profiles (left panel) and dissociation curves (right panel) from quantitative real-time PCR for examining mRNA expression of alkaline phosphatase (ALP) in human articular chondrocytes, in which glyceraldehyde-3-phosphate dehydrogenase (GAPDH) gene acted as a house keeping gene for normalization.

2. Quantitative Real-Time PCR:

Referring to FIG. 4, left panel shows the representative real-time PCR profiles from the quantization of ALP and GAPDH mRNA expressions, and right panel shows the dissociation curves of the PCR products of these two genes.

Table 3 shows the percentage changes of mRNA expression of collagen type II, collagen type X and ALP genes by quantitative real-time PCR. It can be clearly seen from Table 3 that as compared to that of the control cultures, the mRNA expression of collagen type II gene in the Aza-C-treated cultures was significantly decreased on Day 3 ($p<0.01$), Day 7 ($p<0.01$) and Day 14 ($p<0.05$) after Aza-C treatment, whereas the mRNA expression of collagen type X gene in the Aza-C-treated cultures was significantly induced on Day 3 ($p<0.05$), Day 7 ($p<0.01$) and Day 14 ($p<0.05$) after Aza-C treatment. ALP mRNA expression of chondrocytes was significantly induced in Aza-C treated cultures on Day 7 and Day 14 after Aza-C treatment ($p<0.01$).

TABLE 3

Percentage changes of mRNA expression of collagen type II, collagen type X and ALP genes by quantitative real-time PCR

| mRNA | Treatment | Day 3 (%) | Day 7 (%) | Day 14 (%) |
|---|---|---|---|---|
| Collagen type II | Control | 100.0 ± 1.6 | 125.0 ± 1.2 | 10.0 ± 6.3 |
| | Aza-C | 7.3 ± 1.2** | 1.0 ± 0.4** | 3.0 ± 0.9* |
| Collagen type X | Control | 100.0 ± 9.1 | 71.0 ± 17.5 | 159.0 ± 21.8 |
| | Aza-C | 398.0 ± 26.3* | 64,013.0 ± 5.0** | 335.0 ± 1.4* |
| ALP | Control | 100.0 ± 9.3 | 4.0 ± 1.1 | 18.0 ± 4.7 |
| | Aza-C | 175.8 ± 13.5 | 31,900.0 ± 4.7** | 735.6 ± 3.2** |

Data are expressed as mean ± S.E.M.
*$p < 0.05$, as compared to the control culture of the same day after Aza-C treatment.
**$p < 0.01$, as compared to the control culture of the same day after Aza-C treatment.

Figure 5:
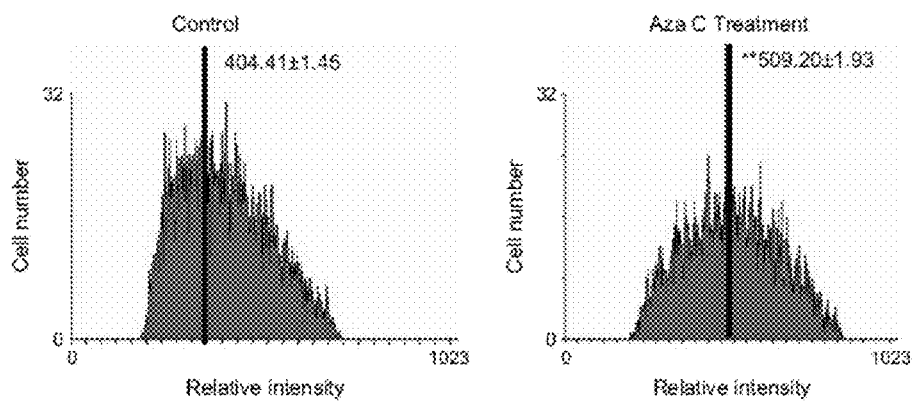
FIG. 5 shows the cell size changes of human articular chondrocytes on Day 14 after a 48 hr treatment of Aza-C, wherein the representative cell size distribution profile was measured from flow cytometry, and the relative intensity represents the cell size of a chondrocyte. Mean±SEM of the relative intensity from the control cultures (404.41±1.45) and Aza-C-treated cultures (509.20±1.93) are shown (Data were evaluated by Student's t-test, and : $p<0.01$, as compared to the control culture)

3. Flow Cytometry:

Referring to FIG. 5, the cell size of articular chondrocytes in Aza-C treated cultures (509.20±1.93) was significantly increased (a 26% increase) as compared to the control cultures (404.41±1.45) on Day 14 after Aza-C treatment ($p<0.01$).

Figure 6:
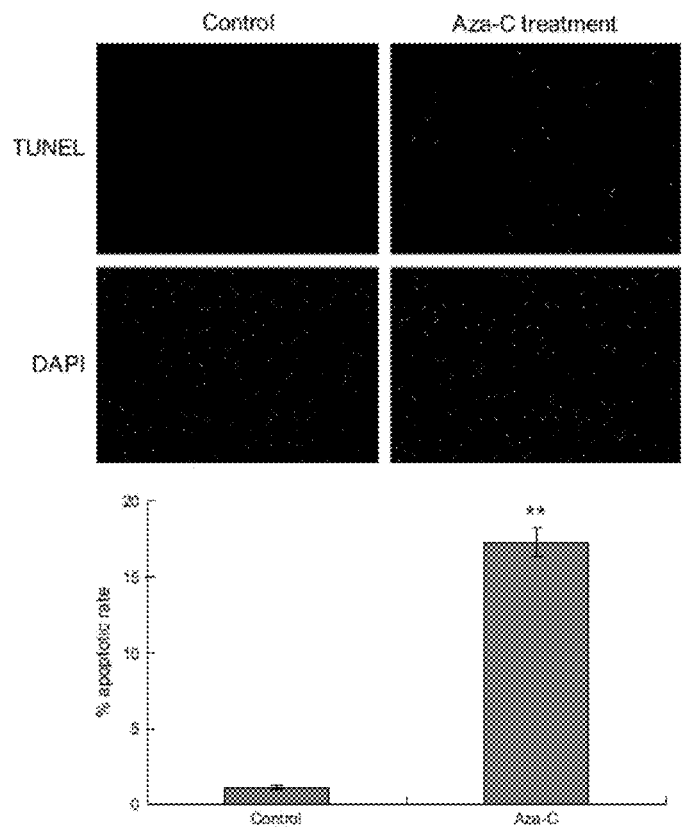
FIG. 6 shows the induction of apoptosis in human articular chondrocytes on Day 14 after a 48 hr treatment of Aza-C, wherein the representative images of the TUNEL stained cells (stained red, defined apoptoic cells) and DAPI counter stained cells (stained blue, defined total cells) are shown (100× magnification). The apoptotic rate of the control and Aza-C-treated cells were compared. Each bar represents the mean±SEM of four replicated cultures (Data were evaluated by Mann-Whitney U test, and : $p<0.01$, as compared to the control culture).

4. TUNEL Assay:

Referring to FIG. 6, as compared to the control cultures, the apoptotic rate of articular chondrocytes in Aza-C-treated cultures was significantly increased on Day 14 after Aza-C treatment ($p<0.01$).

Discussion:

Endochondral bone formation physiologically occurs during the development of embryonic long bones and the postnatal longitudinal bone growth in epiphyseal growth plate. During this process, chondrocytes play important roles according to the temporal and spatial signals in the internal environment of the body. Chondrocytes pass through several stages including proliferation, maturation, hypertrophy, calcification and eventually apoptosis (H. M. Kronenberg (2003), *Nature*, 423:332-336; L. Shum and G. Nuckolls (2002), *Arthritis Res*, 4:94-106). Proliferation and matrix production of chondrocytes result in cartilage enlargement, and the specific marker molecules in this stage are collagen type II and glucosaminoglycan. Thereafter, chondrocytes undergo terminal differentiation: cells stop proliferating, enlarge (hypertrophy), and express collagen type X; subsequently, cells express annexins, Indian hedgehog (Ihh), alkaline phosphatase and deposit mineral; and finally, hypertrophic chondrocytes undergo apoptosis (H. M. Kronenberg (2003), *Nature*, 423:332-336; F. Long et al. (2001), *Development*, 128:5099-5108; K. J. Noonan et al. (1998), *J Orthop Res*, 16:500-508).

It has been reported that hypertrophic chondrocytes play roles in directing the mineralization, vascularization and osteoblastogenesis in the surrounding area via factors secreted from hypertrophic chondrocytes (H. M. Kronenberg (2003), *Nature*, 423:332-336). However, the process of endochondral ossification does not occur in articular chondrocytes, which maintain chondrocytic functions for one's whole life. In OA cartilage, collagen type II that normally exists in articular cartilage was decreased, but the reparative collagen, i.e., collagen type X, was expressed (M. Adam and Z. Deyl (1983), *Clin Chim Acta*, 133:25-32; T. Aigner et al. (1993), *J Clin Invest*, 91:829-837; T. Kirsch et al. (2000), *Osteoarthritis Cartilage*, 8:294-302). It was also reported that OA articular chondrocytes resumed the terminal differentiation that was similar to the epiphyseal growth plate, expressed annexins and ALP, and also promoted mineralization and finally apoptosis (T. Kirsch et al. (2000), *Osteoarthritis Cartilage*, 8:294-302). It was further reported that the decrease of cellularity of articular cartilage was consistent with aging and the occurrence of OA in human subjects (A. Abyad and J. T. Boyer (1992), *Curr Opin Rheumatol*, 4:153-159; C. S. Adams and J. R. Horton-We (1998), *Anat Rec*, 250:418-425; F. J. Blanco et al. (1998), *Arthritis Rheum*, 41:284-289).

Apoptotic chondrocytes were found in the superficial and middle zones of articular cartilage in OA patients (F. J. Blanco et al. (1998), *Arthritis Rheum*, 41:284-289; S. Hashimoto et al. (1998a), *Arthritis Rheum*, 41:1632-1638; S. Hashimoto et al. (1998c), *Arthritis Rheum*, 41:1266-1274; F. Heraud et al. (2000), *Ann Rheum Dis*, 59:959-965; J. R. Horton-We et al. (1998), *Matrix Biol*, 17:107-115; T. Kirsch et al. (2000), *Osteoarthritis Cartilage*, 8:294-302). Researchers suggested that apoptosis of articular chondrocytes might play a very important role in the loss of cellularity of chondrocytes (M. Lotz et al. (1999), *Osteoarthritis Cartilage*, 7:389-391). Subsequently, the decrease of cellularity of articular chondrocytes may result in an inability to maintain the appropriate formation of extracellular matrix, and eventually OA develops (M. Lotz et al. (1999), supra).

Accordingly, several strategies to prevent the progress of OA from the aspect of chondrocyte biology have been suggested, such as blocking apoptosis of chondrocytes (F. J. Blanco et al. (1995), *Am J Pathol*, 146:75-85; S. Hashimoto et al. (1997), *Arthritis Rheum*, 40:1749-1755; F. Heraud et al. (2000), *Ann Rheum Dis*, 59:959-965). Thus, suppressing the terminal differentiation of articular chondrocytes may be a useful strategy to prevent the progress of osteoarthritis. It is worthwhile to test the usefulness of the proposed strategies in cultured chondrocytes before in vivo studies. Therefore, in this invention, the applicants established a terminal differentiation model in cultured human articular chondrocytes that could mimic the biological characteristics of OA chondrocytes.

The results obtained from the above experiments indicated that terminal differentiation of human articular chondrocytes could be induced in a 3-dimensional culture system. It was found that a 48 hr treatment of Aza-C could induce the expressions of collagen type X and suppress that of collagen type II starting from the 3rd day after Aza-C treatment. Subsequently, ALP expression was induced on Day 7 after Aza-C treatment (see the results shown in FIGS. 1-4 and Table 3). Furthermore, hypertrophic human articular chondrocytes and even apoptosis of human articular chondrocytes were also observed on Day 14 after Aza-C treatment (see the results shown in FIGS. 5-6). The down-regulation of the normal functional gene (i.e., collagen type II gene) of articular chondrocytes and the up-regulation of marker genes of hypertrophy (i.e., collagen type X gene) and mineralisation (i.e., ALP gene) of chondrocytes demonstrated that the articular chondrocytes underwent terminal differentiation. The cell enlargement of Aza-C-treated cells analysed by flow cytometry further demonstrated the hypertrophy of articular chondrocytes. Moreover, the increase of apoptotic rate of Aza-C-treated cells indicated that the articular chondrocytes underwent the final process of terminal differentiation. The results obtained from the above experiments demonstrated that in the in vitro culture model of this invention, the genetic and phenotypic properties of human articular chondrocytes could be induced into terminal differentiation.

The results of quantitative real-time PCR from KMU-AC chondrocytes further provided a more promising quantification of mRNA expressions of collagen type II, collagen type X and ALP. While the levels of proteins as expressed by these genes were not determined, the influence of Aza-C upon the mRNA expressions of these genes was proved. Moreover, it has shown that the effects of Aza-C on decreasing collagen type II expression while increasing the expressions of marker genes in the terminal differentiation of articular chondrocytes do not particularly occur in the NHAC-kn chondrocytes. However, the gene expression changes of NHAC-kn and KMU-AC chondrocytes as affected by Aza-C were not consistent with the temporal changes. The maximal effect of Aza-C on gene expressions occurred on Day 7 for KMU-AC and on Day 14 for NHAC-kn. A possible reason for this difference may be the individual variation or age-related reasons. It is therefore suggested that characterizing a temporal profile of gene expression changes as affected by Aza-C be made before using this in vitro terminal differentiation model for articular chondrocytes.

Previous reports indicated that monolayer cultured chondrocytes would undergo dedifferentiation where collagen type II synthesis might be eliminated, whereas the 3-dimensional cultured chondrocytes expressed their differentiation functions like those in vivo (C. Domm et al. (2002), *Osteoarthritis Cartilage*, 10:13-22; J. Malda et al. (2003a), *Biomaterials*, 24:5153-5161; J. Malda et al. (2003b), *Tissue Eng*, 9:939-948). Accordingly, in the studies of this invention, the human articular chondrocytes were cultivated in alginate beads for maintaining their biological characteristics, as they exist in vivo. Therefore, this invention established a novel cell culture model of human articular chondrocytes to mimic the biological characteristics of articular chondrocytes that undergo terminal differentiation. This model could be used to study the molecular and cellular mechanisms of osteoarthritis, to identify a pathology associated with articular chondrocytes (such as osteoarthritis), or to screen a candidate drug used in the treatment of arthritis.

All literature references cited in the present specification are hereby incorporated by reference in their entirety. In case of conflict, the present description, including definitions, will prevail.

While the invention has been described with reference to the above specific embodiments, it is apparent that numerous modifications and variations can be made without departing from the scope and spirit of this invention. It is therefore intended that this invention be limited only as indicated by the appended claims.

We claim:

1. An in vitro three-dimensional culture containing a demethylating agent induced-terminally differentiated human articular chondrocyte for screening a candidate drug for suppressing terminal differentiation of articular chondrocytes, the culture being prepared by a process comprising the steps of:
   (a) admixing normal human articular chondrocytes with an alginate solution to form a cell suspension;
   (b) dropping the cell suspension into a calcium chloride solution to result in the formation of alginate beads which have the normal human articular chondrocytes entrapped therein;
   (c) cultivating the alginate beads in a medium allowing the growth of the entrapped normal human articular chondrocytes; and
   (d) treating the cultivated alginate beads with a demethylating agent to form the in vitro three-dimensional culture containing terminally differentiated human articular chondrocytes, wherein the demethylating agent is selected from the group consisting of 5-azacytidine, 5'-fluoro-2'-deoxycytidine, dihydro-5-azacytidine, 5-aza-deoxycytidine, arabinofuranosyl-5-azacytosine (fazarabine) and pseudoisocytidine.

2. The three-dimensional culture according to claim 1, wherein the normal human articular chondrocytes are obtained from an articular cartilage of a healthy human subject.

3. The three-dimensional culture according to claim 2, wherein the articular cartilage is obtained from a part of the human subject selected from the group consisting of a normal mature knee cartilage, and a cartilage from a metacarpophalargeal, a radiocarpal, an ankle or a pelvic joint.

4. The three-dimensional culture according to claim 3, wherein the articular cartilage is obtained from a normal mature knee cartilage of the human subject.

5. The three-dimensional culture according to claim 1, wherein the alginate solution comprises 1.2% sodium alginate in a 0.9% NaCl solution.

6. The three-dimensional culture according to claim 1, wherein the demethylating agent is 5-azacytidine.

7. The three-dimensional culture according to claim 1, wherein step (c) is performed at 37° C. in a humidified atmosphere of 5% $CO_2$.

8. The three-dimensional culture according to claim 1, wherein step (d) is performed at 37° C. in a humidified atmosphere of 5% $CO_2$.

9. A process for preparing an in-vitro three-dimensional culture containing a demethylating agent induced-terminally differentiated human articular chondrocyte for screening a candidate drug for suppressing terminal differentiation of articular chondrocytes, said process comprising the steps of:
   (a) admixing normal human articular chondrocytes with an alginate solution to form a cell suspension;
   (b) dropping the cell suspension into a calcium chloride solution to result in the formation of alginate beads which have the normal human articular chondrocytes entrapped therein;
   (c) cultivating the alginate beads in a medium allowing the growth of the entrapped normal human articular chondrocytes; and
   (d) treating the cultivated alginate beads with a demethylating agent to form the in vitro three-dimensional culture containing terminally differentiated human articular chondrocytes, wherein the demethylating agent is selected from the group consisting of 5-azacytidine, 5'-fluoro-2'-deoxycytidine, dihydro-5-azacytidine, 5-aza-deoxycytidine, arabinofuranosyl-5-azacytosine (fazarabine) and pseudoisocytidine.

10. The process according to claim 9, wherein the normal human articular chondrocytes are obtained from an articular cartilage of a healthy human subject.

11. The process according to claim 10, wherein the articular cartilage is taken from a part of the human subject selected from the group consisting of a normal mature knee cartilage, and a cartilage from a metacarpophalargeal, a radiocarpal, an ankle or a pelvic joint.

12. The process according to claim 11, wherein the articular cartilage is obtained from a normal mature knee cartilage of the human subject.

13. The process according to claim 9, wherein the alginate solution comprises a 1.2% sodium alginate solution in 0.9% NaCl.

14. The process according to claim 9, wherein the demethylating agent is 5-azacytidine.

15. The process according to claim 9, wherein step (c) is performed at 37° C. in a humidified atmosphere of 5% $CO_2$.

16. The process according to claim 9, wherein step (d) is performed at 37° C. in a humidified atmosphere of 5% $CO_2$.

17. A cell culture model mimicking the terminal differentiation occurring in osteoarthritic chondrocytes, comprising the three-dimensional culture according to claim 1.

18. A kit for identifying a pathology associated with articular chondrocytes, the kit comprising the three-dimensional culture according to claim 1.

19. The kit according to claim 18, wherein the pathology is osteoarthritis.

20. A kit for screening a candidate drug in the treatment of a disorder associated with articular chondrocytes, the kit comprising the three-dimensional culture according to claim 1.

21. The kit according to claim 20, wherein the disorder is osteoarthritis.

* * * * *

SEQUENCE LISTING

```
<160> NUMBER OF SEQ ID NOS: 16

<210> SEQ ID NO 1
<211> LENGTH: 20
<212> TYPE: DNA
<213> ORGANISM: Artificial
<220> FEATURE:
<223> OTHER INFORMATION: RT-PCR forward primer F1 of collagen type
      IIalpha1 gene

<400> SEQUENCE: 1
aactggcaag caaggagaca                                                   20

<210> SEQ ID NO 2
<211> LENGTH: 20
<212> TYPE: DNA
<213> ORGANISM: Artificial
<220> FEATURE:
<223> OTHER INFORMATION: RT-PCR reverse primer R1 of collagen type
      IIalpha1 gene

<400> SEQUENCE: 2
agtttcaggt ctctgcaggt                                                   20

<210> SEQ ID NO 3
<211> LENGTH: 20
<212> TYPE: DNA
<213> ORGANISM: Artificial
<220> FEATURE:
<223> OTHER INFORMATION: RT-PCR forward primer F2 of collagen type
      Xalpha1 gene

<400> SEQUENCE: 3
agccagggtt gccaggacca                                                   20

<210> SEQ ID NO 4
<211> LENGTH: 20
<212> TYPE: DNA
<213> ORGANISM: Artificial
<220> FEATURE:
<223> OTHER INFORMATION: RT-PCR reverse primer R2 of collagen type
      Xalpha1 gene

<400> SEQUENCE: 4
```

```
ttttcccact ccaggagggc                                              20

<210> SEQ ID NO 5
<211> LENGTH: 24
<212> TYPE: DNA
<213> ORGANISM: Artificial
<220> FEATURE:
<223> OTHER INFORMATION: RT-PCR forward primer F3 of alkaline
      phosphatase (ALP) gene

<400> SEQUENCE: 5
gcgaacgtat ttctccagac ccag                                         24

<210> SEQ ID NO 6
<211> LENGTH: 24
<212> TYPE: DNA
<213> ORGANISM: Artificial
<220> FEATURE:
<223> OTHER INFORMATION: RT-PCR reverse primer R3 of alkaline
      phosphatase (ALP) gene

<400> SEQUENCE: 6
ttccaaacag gagagtcgct tcaa                                         24

<210> SEQ ID NO 7
<211> LENGTH: 27
<212> TYPE: DNA
<213> ORGANISM: Artificial
<220> FEATURE:
<223> OTHER INFORMATION: RT-PCR forward primer F4 of 18S rRNA gene

<400> SEQUENCE: 7
ccgcagctag gaataatgga ataggac                                      27

<210> SEQ ID NO 8
<211> LENGTH: 23
<212> TYPE: DNA
<213> ORGANISM: Artificial
<220> FEATURE:
<223> OTHER INFORMATION: RT-PCR reverse primer R4 of 18S rRNA gene

<400> SEQUENCE: 8
acgacggtat ctgatcgtct tcg                                          23

<210> SEQ ID NO 9
<211> LENGTH: 21
<212> TYPE: DNA
<213> ORGANISM: Artificial
<220> FEATURE:
<223> OTHER INFORMATION: quantitative real-time PCR forward primer F5 of
      collagen type IIalpha1 gene

<400> SEQUENCE: 9
caacactgcc aacgtccaga t                                            21

<210> SEQ ID NO 10
<211> LENGTH: 24
<212> TYPE: DNA
<213> ORGANISM: Artificial
<220> FEATURE:
<223> OTHER INFORMATION: quantitative real-time PCR reverse primer R5 of
      collagen type IIalpha1 gene

<400> SEQUENCE: 10
tcttgcagtg gtaggtgatg ttct                                         24
```

-continued

```
<210> SEQ ID NO 11
<211> LENGTH: 25
<212> TYPE: DNA
<213> ORGANISM: Artificial
<220> FEATURE:
<223> OTHER INFORMATION: quantitative real-time PCR forward primer F6 of
      collagen type Xalpha1 gene

<400> SEQUENCE: 11
cagatttgag ctatcagacc aacaa                                               25

<210> SEQ ID NO 12
<211> LENGTH: 25
<212> TYPE: DNA
<213> ORGANISM: Artificial
<220> FEATURE:
<223> OTHER INFORMATION: quantitative real-time PCR reverse primer R6 of
      collagen type Xalpha1 gene

<400> SEQUENCE: 12
aaattcaaga gaggcttcac atacg                                               25

<210> SEQ ID NO 13
<211> LENGTH: 23
<212> TYPE: DNA
<213> ORGANISM: Artificial
<220> FEATURE:
<223> OTHER INFORMATION: quantitative real-time PCR forward primer F7 of
      glyceraldehyde-3-phosphate dehydrogenase (GAPDH) gene

<400> SEQUENCE: 13
tctcctctga cttcaacagc gac                                                 23

<210> SEQ ID NO 14
<211> LENGTH: 22
<212> TYPE: DNA
<213> ORGANISM: Artificial
<220> FEATURE:
<223> OTHER INFORMATION: quantitative real-time PCR reverse primer R7 of
      glyceraldehyde-3-phosphate dehydrogenase (GAPDH) gene

<400> SEQUENCE: 14
ccctgttgct gtagccaaat tc                                                  22

<210> SEQ ID NO 15
<211> LENGTH: 22
<212> TYPE: DNA
<213> ORGANISM: Artificial
<220> FEATURE:
<223> OTHER INFORMATION: quantitative real-time PCR forward primer F8 of
      alkaline phosphatase (ALP) gene

<400> SEQUENCE: 15
ggaggccgaa agtacatgtt tc                                                  22

<210> SEQ ID NO 16
<211> LENGTH: 22
<212> TYPE: DNA
<213> ORGANISM: Artificial
<220> FEATURE:
<223> OTHER INFORMATION: quantitative real-time PCR reverse primer R8 of
      alkaline phosphatase (ALP) gene

<400> SEQUENCE: 16
gaaacatgta ctttcggcct cc                                                  22
```